United States Patent [19]
Landanger et al.

[11] Patent Number: 4,976,713
[45] Date of Patent: Dec. 11, 1990

[54] AIMING DEVICE TO POSITION AT LEAST ONE FIXING COMPONENT OF THE CENTROMEDULLAR NAIL TYPE, THROUGH AN IMPLANT

[75] Inventors: Joël Landanger, La Villeneuve; Jean P. Michel, Rochetaillée, both of France

[73] Assignee: ICP France, France

[21] Appl. No.: 385,375

[22] Filed: Jul. 27, 1989

[30] Foreign Application Priority Data

Jul. 28, 1988 [FR] France ................................ 88 10530

[51] Int. Cl.$^5$ ................................................ A61F 2/00
[52] U.S. Cl. ........................................ 606/62; 606/96; 606/97
[58] Field of Search .......... 128/92 VV, 92 YZ, 303 B

[56] References Cited
U.S. PATENT DOCUMENTS 3,135,263 6/1964 Connelley ...................... 128/303 B
4,483,344 11/1984 Atkov et al. ..................... 128/303 B
4,667,664 5/1987 Taylor et al. ................... 128/92 VV Primary Examiner—Robert A. Hafer
Assistant Examiner—Kerry Owens
Attorney, Agent, or Firm—Eric P. Schellin

[57] ABSTRACT

Aiming device to position at least one fixing component of the centromedullar type, through an implant.

The invention relates to the technical sector of medical sciences.

The device according to the invention comprises a viewing type component (1) mounted in a support (5) capable of movement and adjustment in length, rotation, bending and translation, while being likely to recognize the obliquity of the x-ray by viewing it in order to position the viewfinder (1) very precisely level and in line with the part of the nail which should take the fixing component, the said viewfinder (1) being likely to be replaced by a guiding component likely to position the said fixing component.

9 Claims, 5 Drawing Sheets

Fig. 1
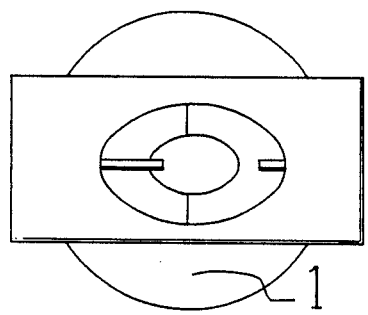
Fig. 2
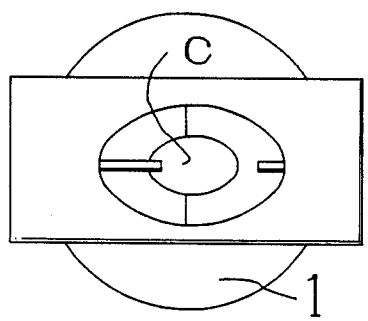
Fig. 3
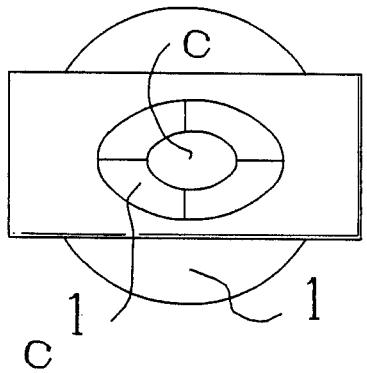
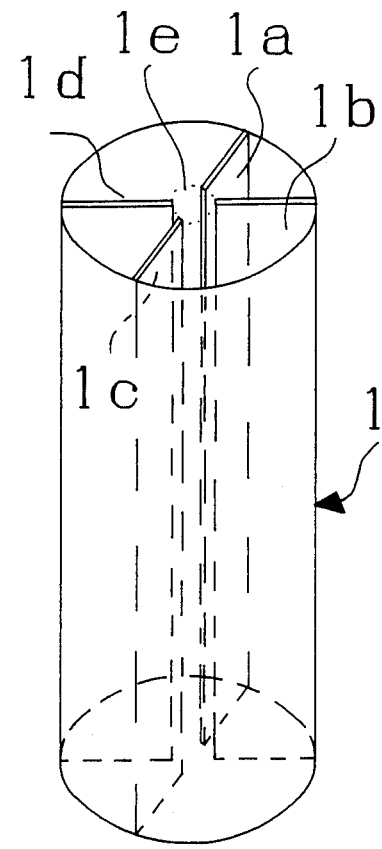
Fig. 4

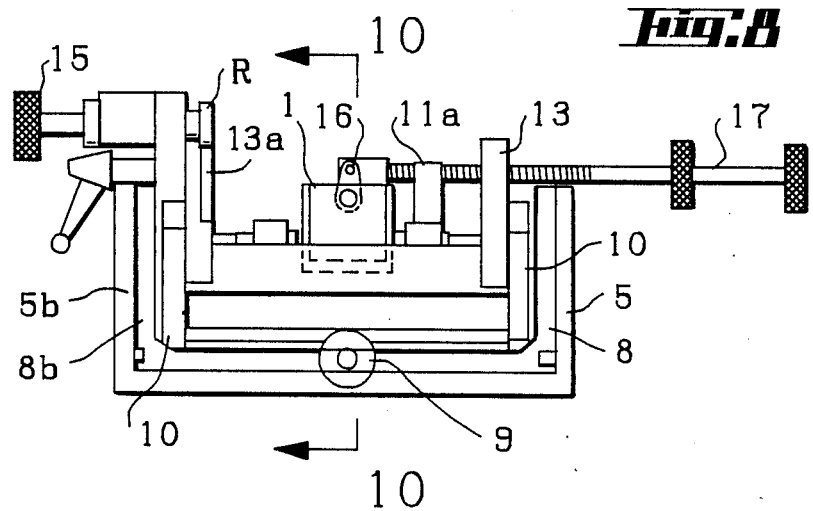
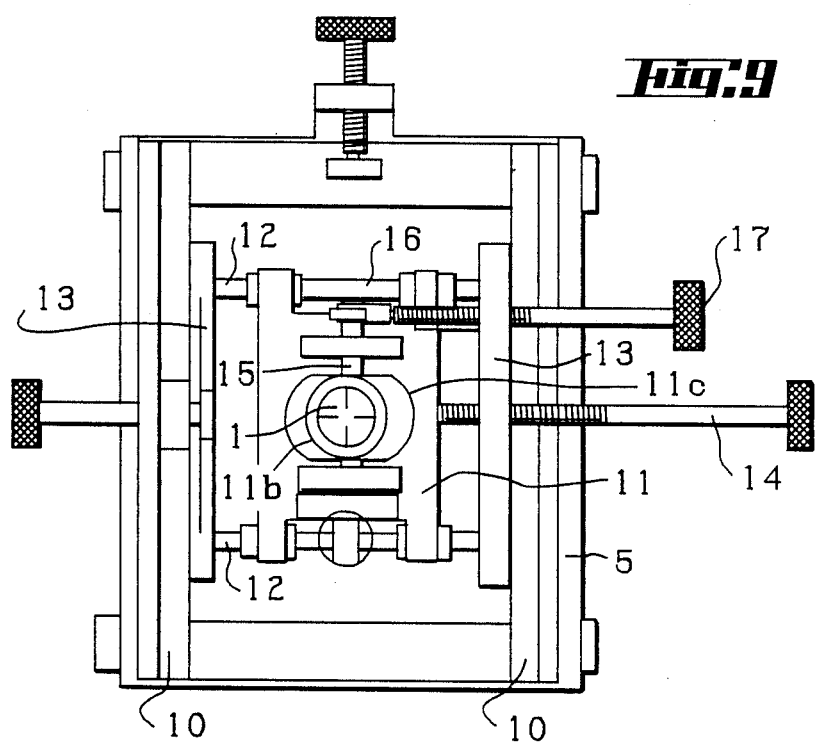

AIMING DEVICE TO POSITION AT LEAST ONE FIXING COMPONENT OF THE CENTROMEDULLAR NAIL TYPE, THROUGH AN IMPLANT

The invention relates to the technical sector of medical sciences.

It is known that nails enhance consolidation by permitting the loads represented by the weight of the body and its kinematic energy applied at the focus of fractures. More and more often, the majority of the nails are locked by means of screws or other fasteners in order to prevent rotations, safely restore lengths and be able to treat a certain amount of epiphysial fractures.

However, the locking technique turns out to be very delicate and requires a unit, known as a "lightness amplifier" which generates x-rays so as to be able to visualise, for example, the hole(s) which have the nails for the passage of the pins or fixing screws.

A significant problem results from the deformation of the nail when it is introduced by twisting or bending. In addition, the nail does not always follow the straight line in its distal part or induces deflection of the distal bone end, thus disturbing the relations and possible marks between the said nail and the bone.

According to a first known locking process, the alignment of the two holes by means of the brightness amplifier is attempted, i.e. one hole which has the nail and one hole which has a viewfinder fixed to the amplifier. In order to obtain the correct result, the image of the hole has to be round. Considering the possible deformations priorly mentioned, very often the hole is ellipsoidal.

Also, problems arise with instability of the amplifier and viewfinder assembly, not integral to the nail. Such handling difficulties require a specially qualified person in order to situate the viewfinder in the centre line of the hole of the nail.

According to another known operational mode, a viewfinder is used which is held by hand, aimed at (again in combination with an x-ray generator) aligning the two holes, i.e. that of the viewfinder and that of the nail. To ensure that this type of mode is efficient, the practitioner has to both correct and integrate the different positions of the space with the movements applied to the viewfinder so as to obtain the concentricity of the holes of the viewfinder and nails and the sphericity of these two holes; once the right position has been found, it still has to be held.

This type of execution can last up to an hour with the corresponding irradiation with x-rays. It is ascertained that this cannot be accepted. In order to overcome these disadvantages, an aiming device comprising a support component on which the viewfinder is mounted as it is, was offered. This state of the art can be illustrated in the U.S. Pat. No. 4,667,664.

However, the result obtained did not appear to be satisfactory. Important problems of adjustment appear considering the means implemented so that the procedure which endeavoured to obtain the different adjustments, particularly when aligning the viewfinder and hole(s) of the implant, did not prove to be a logical operation or deduction.

The invention is aimed at overcoming these disadvantages.

Therefore, the problem brought about is to be able to lock a nail simply and quickly whilst avoiding the maximum of contact with the x-rays.

The aiming device, according to the invention, is designed so as to be adapted to any type of nail and comprises a viewer mounted in a support with a capacity to move and adjust the length, rotation, bending and translation, thereby likely to recognise the obliquity of the x-ray by viewing it in order to position the viewfinder type component in a very precise manner, level and in register with the part of the nail which should take the fixing component.

In order to overcome the problem brought about i.e. to take into consideration possible deformation of the image of the hole of the nail, the viewfinder is designed so as to reduce, by orthographic projection, the three spatial dimensions to a single one whilst being likely to operate correctly even if the part of the implant which should take the fixing component is not strictly round.

In an advantageous manner, the viewfinder is an x-ray transparent cylinder the inside of which is positioned with components made of x-ray opaque steel in particular which, in combination, are likely to delimit a sight. The x-ray opaque steel components are made up of four thin rectangular blades in a cross arrangement whilst being angularly offset by 90°, the said blades being flush with the periphery and the ends of the cylinder whilst delimiting a free central part.

In order to overcome the problem of deformations of the nails following their positioning which thus lose their initial intrinsic relations, the part of the support taking the viewfinder is made up of a mobile assembly mounted so as to move in translation and angular swivelling over a horizontal plane whilst being fitted to positioning locking means, the said mobile assembly taking the viewfinder capable of angular swivelling and locking in position.

In order to overcome the problem brought about i.e. the instability of the viewfinder, part of the support acts as a rail guide cooperating with the fixing component capable of sliding and locking in translation, the said part being mounted capable of angular swivelling with respect to another part of the support taking the viewfinder, whereas the fixing component is designed to cooperate with part of the implant or bone.

The invention is illustrated as follows in more detail by the accompanying drawings, in which:

FIGS. 1 to 3 show the aiming principle according to the invention.

FIG. 4 is a perspective view of an embodiment of the viewfinder.

FIG. 7 is a cross section taken along line 7—7 of FIG. 5.

FIG. 8 is a front view of the part of the support taking the viewfinder.

FIG. 9 is a plan view corresponding to FIG. 8.

Figure 5:
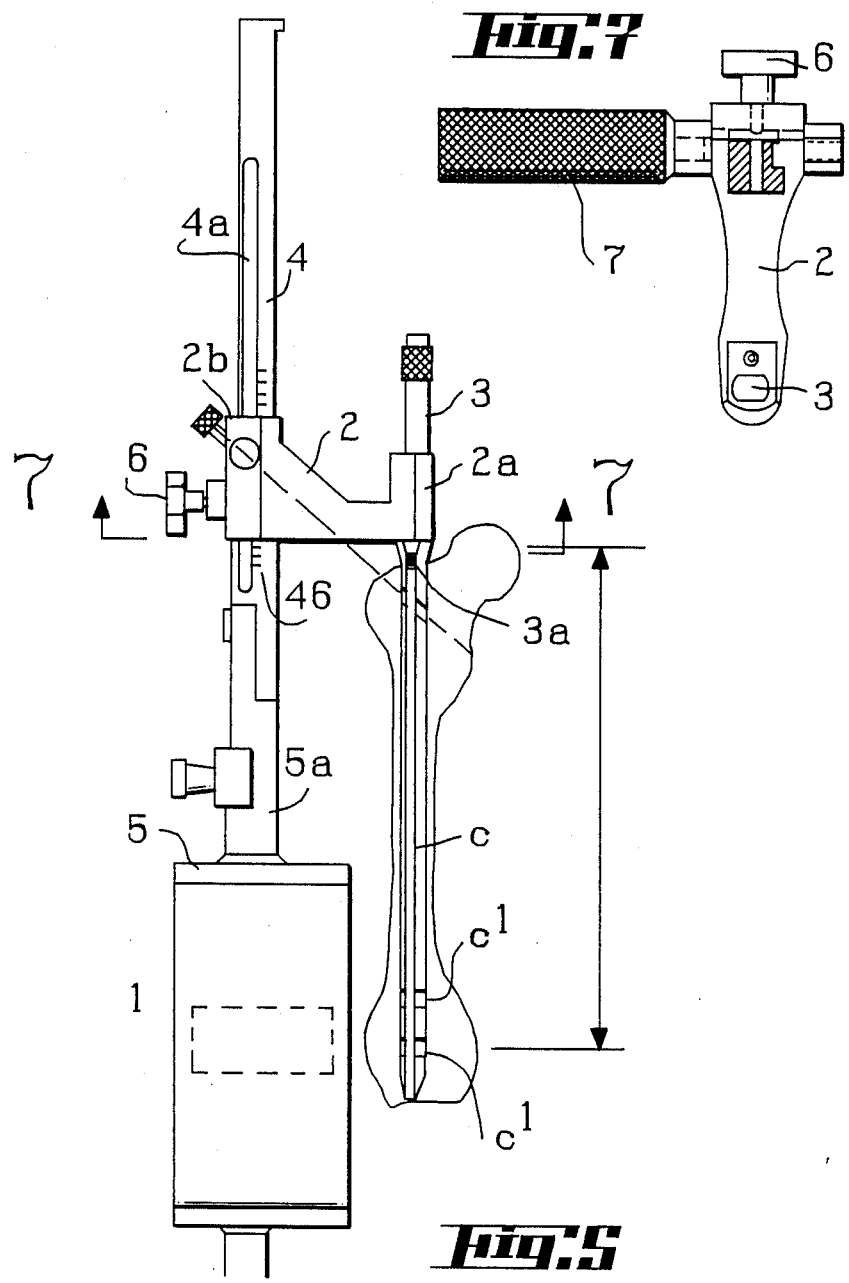
FIG. 5 is a front view of the device.
Figure 6:
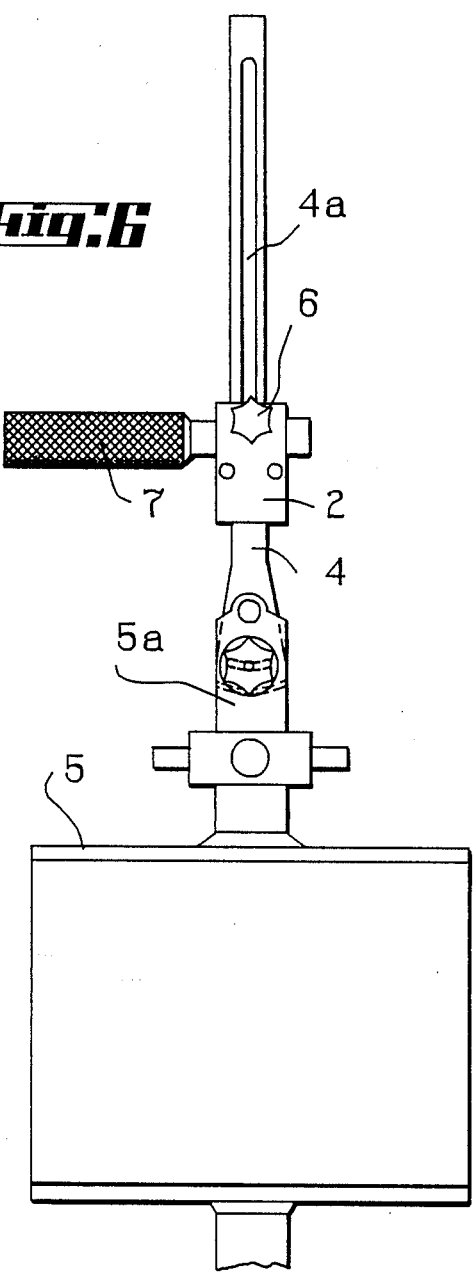
FIG. 6 is a plan view corresponding to FIG. 5.
Figure 10:
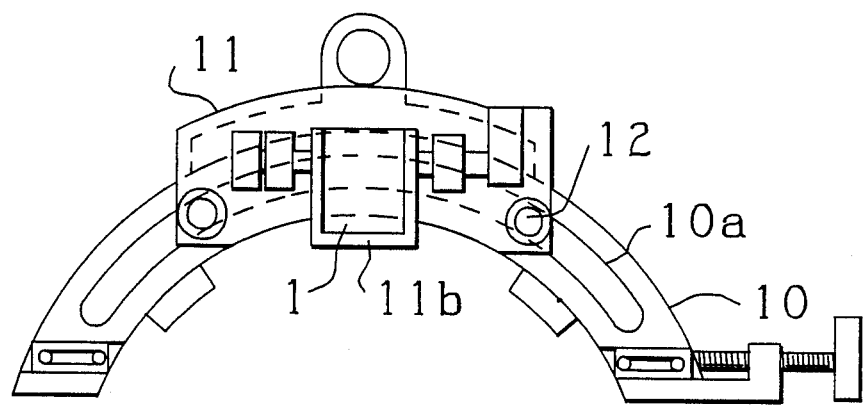
FIG. 10 is a cross section taken along line 10—10 of FIG. 8.
Figure 11:
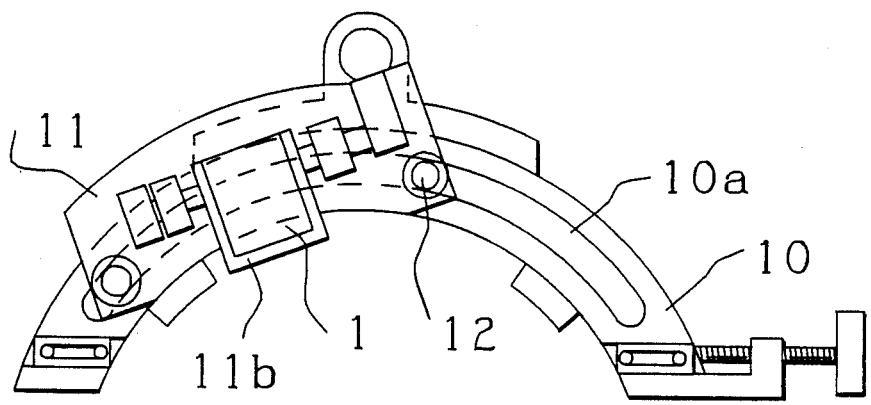
FIG. 11 is a view similar to FIG. 10 showing another position of the mobile assembly.

The device according to the invention comprises a viewfinder (1) mounted in a support (5) capable of moving and swivelling in different directions whilst being likely to recognise the obliquity of the x-ray by viewing it. The viewfinder as such is made up of an x-ray transparent cylinder, circle of x-ray opaque metal or other type, likely to reduce, by orthographic projection, the three spatial dimensions to a single one. In addition, the viewfinder is designed so as to be efficient even if the image of the hole (C1) of the nail (C) is an ellipse shape, which greatly facilitates the adjustment of the brightness amplifier.

In the example illustrated (FIG. 4), the aiming cylinder (1) is x-ray transparent and is fitted internally with four vertical blades (1a), (1b), (1c) and (1d) made of thin x-ray opaque steel. These blades are positioned in orthogonal planes being angularly offset by 90° and flush with the periphery and the ends of the cylinder (1) whilst delimiting a free central part (1e). The dimensions of this central part vary in function of the hole to be aimed and the fixing component to be positioned. Quite obviously, this aiming cylinder may have other configurations such as two rectangular blades on the same diameter or on two different diameters for example.

As indicated, the aiming cylinder enables the obliquity of the x-rays coming from the generator (G) to be determined and acts as a viewfinder at the same time. If the x-ray is perfectly vertical to the cylinder (1), the viewing of the said ray is a cross whose centre (c) is a circle corresponding to the image of the free central part (1e) of the said cylinder. As soon as the x-ray deviates from the vertical line, three visible phenomena occur either in an isolated manner or in combination: thickening of one or several legs of the cross, ovalization of the image of the free central part (1e), overlapping of one of the legs of the cross on the image of the free central part.

This aiming cylinder, an x-ray obliquity detector, due to its characteristics, is therefore capable of perfect movement to the centre of the main ray.

It also enables the obliquity of the ray to be given in degrees thanks to computerized shape analysis.

Therefore it would enable automatic computerized aiming by correct positioning of the viewfinder regardless of the incident x-ray position.

As indicated, once the viewfinder has been placed perfectly perpendicular to the main ray, it appears in the form of a thin lined cross with a white round surface in its centre which corresponds to a "firing line". As this round area has a certain surface variable according to the viewfinder used and corresponding to the cross section of the fixing component to be used, it is situated inside the image viewed and the fixing component will pass very precisely regardless of the shape of the said image. As indicated in the continuation of the description, this aiming cylinder then just has to be changed and replaced by a component likely to direct any cutting, drilling or fixing tool.

Therefore, the aiming cylinder (1) has to be brought to the level of the target made up of the hole (C1) of the nail (C) and the said cylinder positioned level with the main x-ray and the nail deformations considered. A special design of the support (5) results from this.

As shown in FIG. 5, the support (5) cooperates with a fixing component (2) designed so as to be integral with part of the nail (C) or bone. In the example illustrated, the base (2a) of the fixing component (2) is designed so as to be coupled, in a dismantable manner, to the end of the nail (C) projecting beyond the epiphysis of the bone. The base (2a) takes an operating rod (3) with a threaded nose (3a) likely to be screwed into the projecting part of the nail, whilst respecting, in these conditions, the proximal characteristics of each nail.

The upper part of component (2) has a guide tunnel (2b) taking a freely sliding rail (4) coupled in a dismantable manner, capable of angular swivelling, at the end of a part (5a) of a saddle (5) of the support. A slot (4a) made out in the middle part of the rail (4) cooperates with an adjusting screw (6) of element (2) in order to be locked in translation. In addition, marks (4b) are formed on the side of the rail (4) in order to provide lengthwise adjustment of the centre distance (L) between the viewfinder (1) and the fixing component (2) which should correspond to the length between the end of the nail and the locking hole (C1) of the said nail.

A handle (7) is transversally integral with the fixing component (2).

The part of the support (5) taking the viewfinder (1) is made up of a mobile assembly mounted so as to move in translation and swivel angularly over a horizontal plane whilst being fixed to position locking means. This mobile assembly comprises of a mobile saddle (8) transversally mounted with guided sliding inside the fixed saddle (5) whilst being fixed to means of adjustment and locking into position (9). The side plates (5b) and (8b) of the saddles (5) and (8) have profiles in the arc of a circle. Applied against the internal part of the side plates (8b), two fixed components with profiles in the arc of a circle (10) are mounted, each having a semi-circular slot (10a) whose centre corresponds with the centre line of the nail.

The components (10) both take a carriage (11) supported by two parallel guiding rods (12) cooperating with the slots (10a) of the said components. These guiding rods (12) are braced at the end by profiled side plates (13) one of which is designed so as to provide the circular drive of the carriage assembly (11) in combination with the slots (10a) of the components (10).

For example, one of the side plates (13) can have teeth (13a) cooperating with a toothed wheel (R) fixed to an operating component (20) supported by the corresponding component (10). In addition, the carriage (11) is mounted on rods (12) capable of movement and adjustment in translation by means of an operating screw (14) supported by the other side plate (13) and screwed into a boss (11a) of the carriage for example.

The central part of the carriage has a barrel (11b) likely to take the viewfinder (1). This barrel (11b) is supported by two trunnions (15) so as to swivel angularly in a slot (11c) of the carriage, in a plane perpendicular to that of the angular movement of the said carriage (11). The trunnions (5) are fixed to coupling system (16) operated by a screw (17) engaged in a corresponding part of the carriage (11).

Given these conditions, it appears that the viewfinder (1) can be moved and swivelled in every spatial plane, considering the special design of the support such as described. When the aiming is over, after the mobile assembly has been locked, the viewfinder (1) just has to be replaced by any known and suitable component likely to provide guiding for a pin type tool.

It is to be noted that the fixed saddle (5) of the support, takes, in a dismantable manner, a stabilizing system cooperating with the bone in order to suppress the overhang. This system is made up of a horizontal rod (18) integral to the saddle (5) and taking a vertical support rod (19) capable of position adjustment.

In the form of embodiment described and illustrated, the different adjustments are operated by means of knobs without the exclusion of other systems. For example, these knobs can be replaced by square male bushes likely to cooperate with complementary female bushes coupled to a drill type drive component. Remote control adjustment thereby avoiding any irradiation by the x-rays by the practitioner results from this.

It is also anticipated to connect the device to a computer programme, the adjusting knobs being replaced by step motors.

The invention finds a particularly advantageous application for locking centro-medullar nails and more generally, precise aiming through a bone.

We claim:

1. An apparatus for aligning a boring tool with the axis of a perpendicular blind hole in an elongated orthopedic implant, comprising:
   (a) a frame;
   (b) a carriage adjustably mounted to move along an arcuate path on said frame, said arcuate path being an arc of a circle which has an axis coincident with the axis of the implant when said apparatus is used;
   (c) an elongated x-ray optical target means having an optical axis removably mounted in a holder means affixed to the carriage;
   (d) mounting means for mounting the frame in a fixed position relative to the blind hole;
   (e) the holder means being supported by adjustable trunnions whereby the holder means is pivotable along a plane perpendicular to that of the arcuate movement of the carriage;
   whereby the x-ray optical target means as a result of the carriage movement along the arcuate path and the pivotal movement of the holder has its optical axis aligned with the axis of the blind hole.

2. The apparatus of claim 1 wherein the elongated x-ray optical target means is transparent to x-rays and is equally sub-divided by radio opaque relatively thin elongated webs and has an x-ray transparent cylindrical core portion whereby the elongated x-ray optical target means x-ray displays only end edge portions of the elongated webs and a round disc when said elongated x-ray optical means is axially aligned with the axis of the blind hole.

3. Aiming device for the precise and rapid positioning, in combination with a generator of x-rays, of at least one fixation member through an implant, especially of the pin type, placed in the medullary conduit of a bone, comprising a member (1) of the aiming type mounted in a support (5) with the capacity for movement and of control which is capable of recognizing the obliqueness of the x-rays while materializing them in order to position the aimer (1) in alignment with the part of the pin which is to receive the fixation member, whereby the part (5) of the support receiving the aiming member (1) is constituted by a mobile unit which is mounted transversally in a sliding manner, guided inside the fixed part (5) of the support and is subjected to a means of control and of locking in position, which unit (8) receives a carriage (11) mounted with the capacity for movement in translation and of angular movement relative to fixed profiled elements (1), each of which comprises an arcuate aperture (10a) whose center corresponds to the pin axis, which carriage comprises a shaft (11b) very perceptibly in its median part which shaft can receive the aimer (1) and is supported by two pivot spindles (15) for pivoting angularly in an aperture (11c) of the carriage and in a plane perpendicular to that of the circular movement of said carriage, which pivot spindles (15) are subjected to a coupling system which cooperates with a operation and regulation member (17).

4. The device according to claim 3, characterized in that the carriage (11) is carried by two parallel guide shafts (1) which cooperate with the apertures (10a) of the elements (10), which shafts (12) are braced at their end by profiled side plates (13), one of which is designed to permit the circular entrainment of the unit of the carriage (11) in combination with said apertures (10a).

5. The device according to claim 4, characterized in that the carriage (11) is mounted on shafts (12) capable of movement and of control in translation by means of member (14) carried by the other side plate (13) and cooperating with a part of said carriage (11).

6. The device according to claim 3, characterized in that the aiming member (1) is a cylinder radio-transparent to x-rays inside of which elements, especially of radio-opaque steel, are positioned which are constituted by four thin, crossed rectangular blades offset angularly by 90°, which blades contact the periphery and the end parts of the cylinder while delimiting a free central part (1e).

7. The device according to claim 3, characterized in that the support comprises a part (4) functioning as a guide rail cooperating with a fixation element (2) capable of sliding and of locking in translation, which part (4) is mounted with a capacity for angular orientation relative to another part (5a) of the support receiving the aiming member, whereas the element (2) is conformed so as to cooperate with a part of the implant or of the bone.

8. The device according to claim 7, characterized in that the base (2a) of the fixation element (2) is designed to be coupled in a demountable manner to the end of the pin extending especially from the epiphysis of the bone.

9. The device according to claim 7, characterized in that reference marks (4b) are formed on the side of the part of the support functioning as rail (4) in order to permit the regulation of the length of the distance between the aiming member and the fixation element, which should correspond to the length between the end of the pin and the locking part of said pin.

* * * * *